United States Patent
Smith, Jr. et al.

(10) Patent No.: US 6,939,994 B1
(45) Date of Patent: Sep. 6, 2005

(54) PROCESS FOR THE PRODUCTION OF BISPHENOL-A

(75) Inventors: Lawrence A. Smith, Jr., Houston, TX (US); Abraham P. Gelbein, Falls Church, VA (US)

(73) Assignee: Catalytic Distillation Technologies, Pasadena, TX (US)

( * ) Notice: Subject to any disclaimer, the term of this patent is extended or adjusted under 35 U.S.C. 154(b) by 61 days.

(21) Appl. No.: 10/947,684

(22) Filed: Sep. 23, 2004

(51) Int. Cl.$^7$ .............................................. C07C 39/16
(52) U.S. Cl. ....................................................... 568/728
(58) Field of Search ........................................ 568/728

(56) References Cited

U.S. PATENT DOCUMENTS

| | | | |
|---|---|---|---|
| 4,308,404 A | 12/1981 | Kwantes et al. | 568/727 |
| 4,391,997 A | 7/1983 | Mendiratta | 568/727 |
| 4,400,555 A | 8/1983 | Mendiratta | 568/728 |
| 4,471,154 A | 9/1984 | Franklin | 585/864 |
| 5,087,767 A | 2/1992 | Okamoto et al. | 568/727 |
| 5,679,312 A | 10/1997 | Jin et al. | 422/191 |

Primary Examiner—Michael L. Shippe

(57) ABSTRACT

Bisphenol-A (BPA) is efficiently produced from phenol and acetone via countercurrent and multistage contact with a solid acid catalyst in the presence of an agent that enhances the removal of water of reaction from the reaction zone. A preferred contacting device is a distillation column wherein the catalyst is contained within a distillation mass transfer structure. A preferred water removal agent is a $C_6$ hydrocarbon, e.g., n-hexane. The column is configured with a reboiler, reflux condenser, and decanter as reflux drum. Phenol (in excess of the reaction stoichiometry) is fed to the column above the catalyst zone and acetone toward the bottom of the catalyst zone. Hexane is fed directly into the reboiler. Boilup is primarily hexane vapor which as it ascends the column removes water from the reaction zone in the vapor stream while the acetone is maintained within the reaction zone by dissolving in the descending phenol rich liquid stream. The water is removed from the system as decant liquid while the hexane is refluxed to the column. According to the invention nearly 100% conversion of the acetone is achieved and the phenol/BPA/hexane column bottoms product is free of water.

17 Claims, 1 Drawing Sheet

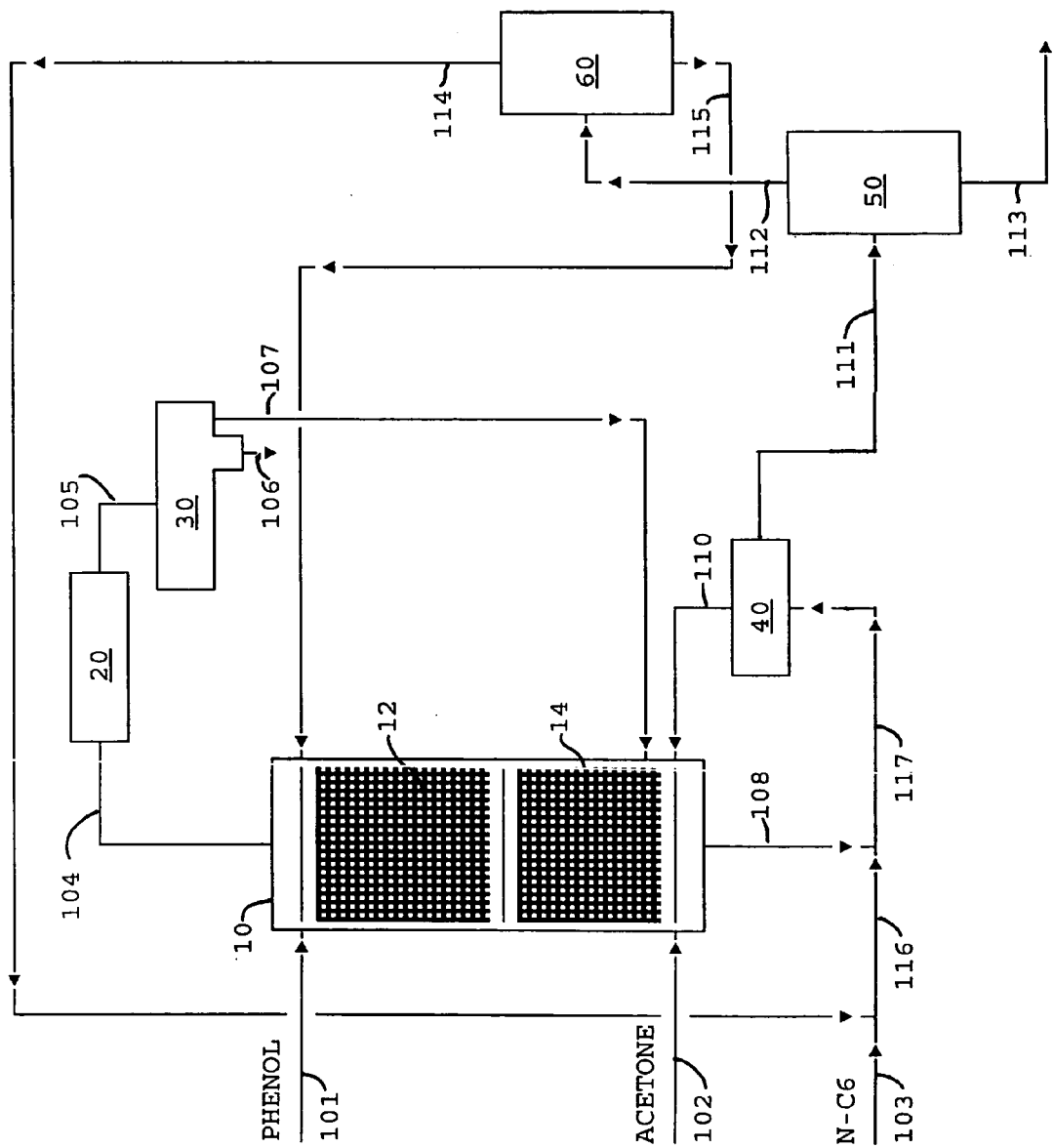

PROCESS FOR THE PRODUCTION OF BISPHENOL-A

BACKGROUND OF THE INVENTION

1. Field of the Invention

The present invention relates to the production of bisphenol-A by the reaction of phenol with acetone. More particularly the invention relates to a process wherein the reaction products, especially water, are separated concurrently with the reaction in a distillation column reactor. More particularly the invention relates to a process wherein the water of reaction is removed by stripping with an inert hydrocarbon vapor produced in the reboiler of a distillation column reactor.

2. Related Information

Bisphenol-A is a basic feedstock or intermediate product for the commercial manufacture of various polymers including the polyarylates, polyamides, polyetherimides, polysulfuones and polycarbonates, etc., epoxy resins and modified phenol-formaldehyde resins, etc. Various processes for producing bisphenol-A from the reaction of phenol with acetone in the presence of an acidic ion-exchange resin catalyst have been disclosed in U.S. Pat. Nos. 4,308,404; 4,391,997; 4,400,555; 4,471,154 and 5,087,767.

The method of carrying out catalytic reactions, wherein the components of the reaction system are concurrently separable by distillation, are described variously in U.S. Pat. Nos. 4,215,011; 4,232,177; 4,242,530; 4,250,052; 4,302,356; and 4,307,254 commonly assigned herewith. Briefly, structures which serve as both catalyst site and distillation structure are then disposed in the distillation column reactor. A variety of catalyst structures for this use are disclosed in commonly assigned U.S. Pat. Nos. 4,443,559; 4,536,373; 5,057,468; 5,130,102; 5,133,942; 5,189,001; 5,262,012; 5,266,546; 5,348,710; 5,431,890; and 5,730,843 which are incorporated herein. These structures have been particularly well adapted for use with acidic ion-exchange resins. The method is commonly known as catalytic distillation and has been successfully adapted in various forms for many reactions, including etherification of olefins with alcohols (U.S. Pat. No. 4,302,254), selective hydrogenation (U.S. Pat. No. 6,169,218B1), hydrodesulfurization (U.S. Pat. No. 5,779,883), isomerization (U.S. Pat. No. 6,495,732) and aromatic alkylation (U.S. Pat. No. 4,849,569).

A catalytic distillation column reaction is a benefit first, because the reaction is occurring concurrently with distillation, the initial reaction products and other stream components are removed from the reaction zone as quickly as possible reducing the likelihood of side reactions. Second, because all the components are boiling the temperature of reaction is controlled by the boiling point of the mixture at the system pressure. The heat of reaction simply creates more boil up, but no increase in temperature at a given pressure. As a result, a great deal of control over the rate of reaction and distribution of products can be achieved by regulating the system pressure.

U.S. Pat. No. 5,679,312 discloses producing bisphenol-A by carrying out the reaction by feeding phenol and acetone concurrently downflow in a distillation column reactor having acidic ion exchange resin catalysts held on trays by screens. An inert stripping gas, e.g., nitrogen or argon, is fed in the bottom of the distillation column reactor to aid in removing the water of reaction. With its concurrent feed of the phenol and acetone the patentee gets only about 96% conversion of the acetone. The patentee exhibited a lack of skill and knowledge in regard to catalytic distillation and its areas of significant commercial use as well as being unable to envision how a catalytic distillation system could be used to carry out the reaction of acetone with phenol to produce bisphenol-A.

It is an advantage of the present invention that the catalytic distillation system, with its inherent benefits is employed for the production of bisphenol-A from the condensation reaction of phenol and acetone. It is a further advantage that an inert hydrocarbon serves to remove water of reaction from the reaction system and is easily reused by return to the reaction system. It is a further advantage that substantially all of the acetone is trapped in the reaction zone and near 100% conversion is obtained.

SUMMARY OF THE INVENTION

Bisphenol-A is efficiently produced from the condensation of phenol and acetone via countercurrent and multistage contact with a solid acid catalyst in the presence of stripping medium which is inert under the reaction conditions and boiling in the range of 50 to 90° C. at the pressure in the column, preferably inert hydrocarbons, which includes aliphatic hydrocarbons such as normal hexane. A preferred contacting system is a distillation column reactor where the catalyst is contained within a distillation mass transfer structure. A preferred water removal agent is a $C_6$ hydrocarbon, e.g., normal hexane.

In the present invention the stripping medium is one that is inert and which has both a liquid and vapor state in the reactor, i.e., boiling, such that the vapors strip the water from the reaction mixture and are condensed along with the water and separated therefrom. Preferably the stripping medium is not soluble to any substantial degree with water, so the separation can be made by decanting. The preferred mode of operation is that characterized by a distillation condition existing within the reaction zone. The present invention is carried out in a catalyst-packed column which can be appreciated to contain a vapor phase and some liquid phase as in any distillation. The distillation column reactor is operated at a pressure such that the reaction mixture (or components thereof) is boiling in the column and/or in the bed of the catalyst (distillation conditions). As in any distillation there is a temperature profile along the column. At some point along the column or catalyst bed a component of the reaction mixture may be a liquid and a vapor at a higher temperature point in the column, thus creating an internal reflux, whereas some of the vaporized material in the column, e.g. water and the stripping medium is removed as a vapor.

A preferred embodiment of the invention may be described as a process for the reaction of phenol with acetone to produce bisphenol-A comprising:

(a) feeding a stoichiometric excess of phenol to a catalyst zone which preferably comprises a bed of solid acidic catalyst, such as ion-exchange resin, in a distillation column reactor and (b) feeding acetone toward the bottom of said catalyst zone;

(c) providing a hydrocarbon, which is inert under the reaction conditions and boiling in the range of 50 to 90° C. at the pressure in the distillation column reactor, in a state of distillation comprising both a vapor and liquid thereof within said distillation column reactor;

(d) concurrently in said distillation column reactor
  (i) contacting said acetone and phenol in the presence of said acidic catalyst under conditions of temperature and pressure to form a reaction mixture containing unreacted acetone, unreacted phenol, bisphenol-A, and water, whereby said acetone is dissolved in said phenol such that substantially all of said acetone is converted to bisphenol-A;

(ii) stripping said water from said reaction mixture utilizing said hydrocarbon vapor;

(e) removing said bisphenol-A and unreacted phenol from the distillation column reactor as bottoms;

(f) removing said water and hydrocarbon vapor from the distillation column reactor as overheads; and (g) condensing said overheads and separating the condensed inert hydrocarbon from the condensed water.

In a preferred process the additional steps are:

(h) recycling the condensed hydrocarbon to said distillation column reactor;

(i) flashing said bottoms to separate said unreacted phenol from said bisphenol-A; and (j) condensing the separated phenol and recycling the condensed separated phenol to near the top of said distillation column reactor.

BRIEF DESCRIPTION OF THE DRAWING

The FIGURE is a flow diagram of a preferred reactor system employed in the instant invention.

DETAILED DESCRIPTION OF THE PREFERRED EMBODIMENT PROCESS

Bisphenol-A is formed via the reaction of two moles of phenol with one mole acetone:

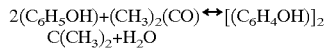

The equilibrium constant for this reaction is small (K=0.8 mole fraction basis).

The reaction is generally catalyzed by acidic ion exchange resins and is conventionally carried out in the presence of a large stoichiometric excess of phenol which enhances the conversion of acetone and minimizes the production of by-products. However, at practical phenol/acetone charge ratios single stage conversion of phenol is small. For example, at a charge composition of 20/1 molar phenol/acetone, phenol conversion is only 12% while acetone conversion is 92%.

Previously the bisphenol-A was recovered from the reaction mixture via crystallization of a bisphenol-A/phenol adduct. Feed to the crystallizer usually contains on the order of 20 wt. % bisphenol-A. This concentration is obtained by allowing the bisphenol-A to build up in the reaction mixture by using more than one reaction stage with intermediate removal of water via vacuum of inert gas stripping between the stages. In so doing the unreacted phenol and acetone and the water distribute between the overhead product streams and the bottoms stream containing the BPA product. In conventional processing the phenol, acetone and water are subsequently separated in downstream distillation columns.

The present invention simplifies the overall processing scheme by combining reaction and separation steps. This is accomplished by performing the reaction in a multistage distillation column reactor configured with structured packing containing the catalyst and which operates with an inert stripping medium fed to the reboiler of the column that preferentially removes the water of reaction from the reaction zone. The water is removed in the distillate stream from the column.

The countercurrent feed of the present invention provides another advantage in that by feeding liquid phenol to the column above the reaction zone, acetone is removed from the ascending vapor stream and returns to the reaction zone. The net effect is to "trap" the acetone within the reaction zone where it reacts essentially to completion.

The stripping medium (preferably inert hydrocarbons) has the additional function of controlling the reboiler temperature and the temperature profile in the lower portion of the reaction zone which is preferably in the 70–80° C. range. The inert hydrocarbon has the additional advantage of being readily separable from the water in the distillate stream via decantation. The inert hydrocarbon layer from the decanter is preferably returned to the column. Thus a constant feed of the inert stripping medium is not necessary and makeup can be added as required.

Catalysts

The reaction of phenol and acetone to produce bisphenol-A is catalyzed by acidic catalysts, preferably cation exchange resins. Suitable acid cation exchange resins include those which contain sulfonic acid groups, and which may be obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinyl phenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymers which already contain sulfonic acid groups; for example, by treatment with fuming sulfuric acid, i.e., sulfuric acid which contains sulfur trioxide. The treatment with fuming sulfuric acid is preferably carried out at 0 to 150° C. and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification 908,240). The ion exchange resin is generally used in a granular size of about 0.25 to 1 mm, although particles from 0.15 mm up to about 2 mm may be employed. The finer catalysts provide high surface area, but also result in high pressure drops through the reactor. The macroreticular form of these catalysts have much larger surface area exposed and limited swelling which all of these resins undergo in a non-aqueous hydrocarbon medium compared to the gelular catalysts.

The container employed to hold the catalyst particles may have any configuration, such as the pockets disclosed in the patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component forms the catalytic distillation structure. The total volume of open space for the catalytic distillation structure should be at least 10 volume % and preferably at least 20 volume % up to about 65 volume %. Thus, desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire or an expanded aluminum. Other resilient components may be similar open mesh knitted polymeric filaments of nylon, teflon and the like. Other materials such as highly open structures foamed material, e.g., reticulated polyurethane foam (rigid or resilient) may be formed in place or applied around the catalyst component.

In the case of larger catalyst components such as from about ¼ inch to ½ pellets, spheres, pills and the like, each such larger component may be individually intimately associated with or surrounded by the spacing component as described above.

It is not essential that the spacing component entirely cover the catalyst component. It is only necessary that the spacing component intimately associated with the catalyst component serve to space the various catalyst components away from one another as described above. Thus, the spacing component provides in effect a matrix of substantially open space in which the catalyst components are randomly but substantially evenly distributed.

A preferred distillation structure is described in U.S. Pat. No. 5,730,843 noted above, which comprises at least two wire mesh tubes arrayed in a substantially parallel, adjacent and vertically aligned row and at least one offset wire mesh tube disposed adjacent to and spaced from said vertically aligned wire mesh tubes. In a more preferred embodiment the distance between the vertically aligned tubes of the columns is sufficient to allow the offset wire mesh tube to overlap the vertically aligned wire mesh tubes without contacting said vertically aligned wire mesh tubes to thereby form a tortuous fluid pathway.

Referring now to the FIGURE a flow diagram of a preferred reactor system is shown. The distillation column reactor 10 is seen to contain beds of catalyst 12 and 14 which comprise a reaction zone having 50 equilibrium stages with 4 trays above the reaction zone and 4 trays below the reaction zone. Stage 1 is the condenser 20 and stage 60 is the reboiler 40. Phenol is fed via flow line 101 above stage 3 and acetone is fed via flow line 102 above stage 40. The acetone and phenol react in the reaction zone to produce a reaction mixture containing phenol, acetone, bisphenol-A and water. N-hexane recycle is fed via flow line 103, combined with n-hexane recycle 114 to the reboiler 40 through flow lines 116, 117, and 110 eventually to the bottom of the distillation column reactor 10 at about stage 59. The n-hexane strips the water of reaction out as it is formed and removes it as overheads via flow line 104. The overheads are condensed in condenser 20 and collected in receiver/decanter 30 where the water is separated and removed via flow line 106. N-hexane (containing a small amount of acetone) is taken from the receiver/decanter 30 via flow line 107 and returned to the distillation column reactor 10 at about stage 56. The water contains about 2% acetone which corresponds to about 99.5% conversion. The bottoms product containing phenol, bisphenol-A and only trace amounts of water and acetone is removed from the distillation column reactor 10 via flow line 111 from reboiler 40.

The bottoms product removed via flow line 111 is flashed to 3 psi in flash drum 50 producing a n-hexane rich vapor stream in flow line 112 and a phenol/bisphenol-A liquid stream in flow line 113. The n-hexane rich vapor stream in flow line 112 is cooled (not shown) and passed to knock out chamber 60 where any liquid is removed via flow line 115 before compressing (not shown) and recycling via flow line 114. A recycle stream from the recovery section (not shown) is also fed to chamber 60 via line 116. Liquid from the knock out chamber 60 in flow line 115 contains essentially phenol and is recycled to distillation column reactor above stage 3. The phenol/bisphenol-A liquid stream in flow line 113 is combined and sent to the bisphenol-A recovery system where the bisphenol-A is recovered by crystallization. In the operation of this process the normal hexane or other stripping medium is recovered and recycled. The only feed of this component to the column is at startup and for makeup of that lost during the recovery.

The recovery of the bisphenol-A is summarily described as follows:

The phenol/bisphenol-A stream is combined with other phenol rich recycle streams from the crystallization systems and is sent to an evaporator system operating at ~2 psi. The resulting vapor is partially condensed producing a hexane-rich recycle and phenol rich liquid recycle. The liquid product from the evaporator containing 29 wt. % bisphenol-A is fed to a crystallization system which generates a slurry of bisphenol-A/phenol adduct in phenol. The slurry is centrifugally separated into a mother liquor stream which is cycled to the evaporation system and a solid adduct stream which is wet with phenol for further processing to recover phenol for recycle.

The solid adduct stream is combined with net feed liquid phenol stream and heated to resolution temperature. The resulting solution stream is sent to a second crystallization system producing a slurry stream which is separated into further purified adduct stream and mother liquor stream. The latter is cycled to the evaporator feed tank.

The phenol wet solid is melted and fed to a second vacuum evaporation system to dephenolate the adduct and product bisphenol-A melt product stream which contains a small amount of phenol. The phenol vapor stream is condensed and sent to the phenol recycle tank. The combined phenol recycle stream is fed to the catalytic distillation column via stream 101.

Final purification of the bisphenol-A is via hexane stripping to remove residual phenol and steam stripping to remove residual hexane. The recovered hexane streams are recycled to the CD column. The purified bisphenol-A melt is pelletized or flaked and finally bagged.

EXAMPLE

The following example demonstrates use of the invention for reacting phenol with acetone to produce bisphenol-A. Equipment and stream names are as given in the FIGURE. Compositions and stream flows, and conditions are in the Table.

Main reaction in reactor 10 is the following reaction catalyzed by a supported acidic cation exchange resin supported in a mass exchange distillation structure: 2 Phenol+Acetone↔Bisphenol-A+Water

TABLE

|  | 101 | 102 | 103 | 107 | 112 | 113 | 114 | 115 | 116 |
|---|---|---|---|---|---|---|---|---|---|
| Temperature F. | 150 | 150 | 100 | 122.2 | 109 | 180.4 | 109.3 | 109.5 | 108.9 |
| Pressure psi | 20 | 20 | 25 | 25 | 3 | 3 | 25 | 25 | 25 |
| Vapor Frac | 0 | 1 | 0 | 0 | 0.898 | 0 | 0 | 0 | 0 |
| Mass Flow lb/hr |  |  |  |  |  |  |  |  |  |
| PHENOL | 144,349 | 0 | 0 | 2 | 7,206 | 129,185 | 611 | 6,597 | 611 |
| ACETONE | 147 | 8,712 | 0 | 14 | 12 | 29 | 4 | 8 | 4 |
| BISPHENO | 0 | 0 | 0 | 0 | 0.003 | 18,391 | 0 | 0.003 | 0 |
| WATER | 0 | 0 | 0 | 3.642 | 0 | 0 | 0 | 0 | 0 |
| N-HEXANE | 2,504 | 0 | 2,546 | 9,109 | 57,761 | 5,168 | 57,366 | 513 | 59,912 |
| Mole Flow lbmol/hr |  |  |  |  |  |  |  |  |  |
| PHENOL | 1,533.8 | 0 | 0.0 | 0.026 | 76.6 | 1,372.7 | 6.5 | 70.1 | 6.5 |
| ACETONE | 2.54 | 150 | 0 | 0.237 | 0.202 | 0.492 | 0.069 | 0.132 | 0.069 |
| BISPHENO | 0 | 0 | 0 | 0 | 0 | 80.561 | 0 | 0 | 0 |
| WATER | 0 | 0 | 0 | 0.202 | 0 | 0 | 0 | 0 | 0 |
| N-HEXANE | 29.06 | 0.00 | 29.55 | 105.70 | 670.26 | 59.97 | 665.68 | 5.95 | 695.22 |
| MWMX | 93.907 | 58.08 | 86.177 | 85.987 | 86.983 | 100.928 | 86.251 | 93.43 | 86.248 |

The invention claimed is:

1. A method of producing bisphenol-A by the reaction of phenol and acetone with the production of bisphenol-A and water in countercurrent and multistage contact with a solid acid catalyst in the presence of stripping medium boiling in the range of 50 to 90° C. at the condition of pressure of the condensation and which is inert under the reaction conditions, whereby the stripping medium removes water from the reaction and acetone is dissolved in the phenol.

2. The method according to claim 1 wherein said stripping medium comprises inert hydrocarbons.

3. The method according to claim 1 wherein said stripping medium comprises aliphatic hydrocarbons.

4. The method according to claim 1 wherein said stripping medium comprises normal hexane.

5. The method according to claim 1 wherein said catalyst is contained within a distillation mass transfer structure.

6. A process for the production of bisphenol-A comprising the steps of:
   (a) feeding phenol to near the top of a distillation column and acetone to near the bottom of said distillation column reactor, said distillation column reactor containing a bed of acidic ion-exchange resin;
   (b) providing to the bottom of said distillation column reactor an inert stripping stream which boils under the conditions of temperature and pressure in said distillation column reactor;
   (c) concurrently in said distillation column reactor
      (i) contacting said acetone and phenol in the presence of said acidic ion-exchange resin to form a reaction mixture containing unreacted acetone, unreacted phenol, bisphenol-A, and water; and
      (ii) trapping said acetone within said distillation column reactor by said phenol whereby substantially all of said acetone is converted to bisphenol-A;
      (iii) stripping said water from said reaction mixture utilizing said inert stripping stream;
   (d) removing said unreacted phenol and bisphenol-A from said distillation column reactor as bottoms; and
   (e) removing said water and inert stripping stream from said distillation column reactor as overheads.

7. The process according to claim 6 wherein said inert stripping stream is present as a liquid which boils at the reaction temperature of phenol and acetone.

8. The process according to claim 6 wherein said bottoms is flashed to separate said unreacted phenol as a vapor from said bisphenol-A and said separated phenol is condensed and recycled to near the top of said distillation column reactor.

9. The process according to claim 8 wherein any unreacted acetone contained within said bottoms is separated from said bisphenol-A as a vapor along with said unreacted phenol and said condensed phenol is flashed again to remove the unreacted acetone as a vapor, said unreacted acetone being recycled to said distillation column reactor.

10. A process for the reaction of phenol with acetone to produce bisphenol-A comprising:
   (a) feeding a stoichiometric excess of phenol to a catalyst zone which preferably comprises a bed of solid acidic catalyst, such as ion-exchange resin, in a distillation column reactor and
   (b) feeding acetone toward the bottom of said catalyst zone;
   (c) providing a hydrocarbon, which is inert under the reaction conditions and boiling in the range of 50 to 90° C. at the pressure in the distillation column reactor;
   (d) concurrently in said distillation column reactor:
      (i) contacting said acetone and phenol in the presence of said acidic catalyst under conditions of temperature and pressure to form a reaction mixture containing unreacted acetone, unreacted phenol, bisphenol-A, and water, whereby said acetone is dissolved in said phenol whereby substantially all of said acetone is converted to bisphenol-A;
      (ii) stripping said water from said reaction mixture utilizing said hydrocarbon vapor;
   (e) removing said bisphenol-A and unreacted phenol from the distillation column reactor as bottoms; and
   (f) removing said water and hydrocarbon vapor from the distillation column reactor as overheads.

11. The process according to claim 10 comprising:
   (g) condensing said overheads and separating the condensed inert hydrocarbon from the condensed water;
   (h) recycling the condensed hydrocarbon to said distillation column reactor;
   (i) flashing said bottoms to separate said unreacted phenol from said bisphenol-A; and
   (j) condensing the separated phenol and recycling the condensed separated phenol to near the top of said distillation column reactor.

12. A process for the production of bisphenol-A comprising the steps of:
(a) feeding acetone and phenol to a distillation column reactor containing a bed of acidic ion-exchange resin and comprising a reboiler;
(b) feeding a $C_6$ hydrocarbon to said reboiler to vaporize a portion of said $C_6$ stream;
(c) concurrently in said distillation column reactor
   (i) contacting said acetone and phenol in the presence of said acidic ion-exchange resin to form a reaction mixture containing unreacted acetone, unreacted phenol, bisphenol-A, and water; and
   (ii) stripping said water from said reaction mixture utilizing said vaporized $C_6$ hydrocarbon;
(d) removing said unreacted phenol and bisphenol-A from said distillation column reactor as bottoms; and
(e) removing said water and vaporized $C_6$ hydrocarbon from said distillation column reactor as overheads.

13. The process according to claim 12 wherein said phenol is fed above said bed of acidic ion-exchange resin and said acetone is fed below said bed of acidic ion-exchange resin such that said acetone is trapped within said distillation column reactor and substantially all of said acetone is converted to bisphenol-A.

14. The process according to claim 12 wherein said overheads are condensed and said $C_6$ hydrocarbon is separated from said water and the separated $C_6$ hydrocarbon is recycled to near the bottom of said distillation column reactor.

15. The process according to claim 12 wherein said bottoms is flashed to separate said unreacted phenol as a vapor from said bisphenol-A and said separated phenol is condensed and recycled to near the top of said distillation column reactor.

16. The process according to claim 15 where any unreacted acetone contained within said bottoms is separated from said bisphenol-A as a vapor along with said unreacted phenol and said condensed phenol is flashed again to remove the unreacted acetone as a vapor, said unreacted acetone being recycled to said distillation column reactor.

17. A process for the production of bisphenol-A comprising the steps of:
(a) feeding phenol to near the top of a distillation column and acetone to near the bottom of said distillation column reactor, said distillation column reactor containing a bed of acidic ion-exchange resin and comprising a reboiler;
(b) providing a $C_6$ hydrocarbon to said reboiler to vaporize a portion of said $C_6$ stream;
(c) concurrently in said distillation column reactor
   (i) contacting said acetone and phenol in the presence of said acidic ion-exchange resin to form a reaction mixture containing unreacted acetone, unreacted phenol, bisphenol-A, and water; and
   (ii) trapping said acetone within said distillation column reactor by said phenol such that substantially all of said acetone is converted to bisphenol-A;
   (iii) stripping said water from said reaction mixture utilizing said vaporized $C_6$ hydrocarbon;
(d) removing said unreacted phenol and bisphenol-A from said distillation column reactor as bottoms;
(e) removing said water and vaporized $C_6$ hydrocarbon from said distillation column reactor as overheads;
(f) condensing said overheads and separating the condensed $C_6$ hydrocarbon from the condensed water;
(g) recycling the condensed $C_6$ hydrocarbon to near the bottom of said distillation column reactor;
(h) flashing said bottoms to separate said unreacted phenol from said bisphenol-A; and
(i) condensing the separated phenol and recycling the condensed separated phenol to near the top of said distillation column reactor.

* * * * *